United States Patent
Dubois

(10) Patent No.: US 9,023,626 B2
(45) Date of Patent: May 5, 2015

(54) METHODS FOR THE SYNTHESIS OF FATTY DIACIDS BY THE METATHESIS OF UNSATURATED DIACIDS OBTAINED BY FERMENTATION OF NATURAL FATTY ACIDS

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 667 days.

(21) Appl. No.: 12/678,366

(22) PCT Filed: Sep. 17, 2008

(86) PCT No.: PCT/FR2008/051664
§ 371 (c)(1),
(2), (4) Date: Mar. 16, 2010

(87) PCT Pub. No.: WO2009/047444
PCT Pub. Date: Apr. 16, 2009

(65) Prior Publication Data
US 2010/0196973 A1   Aug. 5, 2010

(30) Foreign Application Priority Data

Sep. 20, 2007   (FR) ...................................... 07 57691

(51) Int. Cl.
| C12P 7/62 | (2006.01) |
| C12N 1/14 | (2006.01) |
| C07C 67/303 | (2006.01) |
| C07C 51/353 | (2006.01) |
| C07C 51/36 | (2006.01) |
| C07C 67/333 | (2006.01) |
| C07C 67/343 | (2006.01) |
| C12P 7/44 | (2006.01) |

(52) U.S. Cl.
CPC ............. *C07C 67/303* (2013.01); *C07C 51/353* (2013.01); *C07C 51/36* (2013.01); *C07C 67/333* (2013.01); *C07C 67/343* (2013.01); *C12P 7/44* (2013.01); *C12P 7/62* (2013.01)

(58) Field of Classification Search
None
See application file for complete search history.

(56) References Cited

U.S. PATENT DOCUMENTS

| 3,823,070 | A | 7/1974 | Minato et al. | |
| 3,912,586 | A | 10/1975 | Kaneyuki et al. | |
| 4,474,882 | A | 10/1984 | Kunishige et al. | |
| 5,254,466 | A | 10/1993 | Picataggio et al. | |
| 6,506,944 | B1 * | 1/2003 | Schwab et al. | 568/459 |
| 6,569,670 | B2 | 5/2003 | Anderson et al. | |
| 6,660,505 | B2 * | 12/2003 | Staley | 435/136 |

FOREIGN PATENT DOCUMENTS

GB    2043052    10/1980

OTHER PUBLICATIONS

Eschenfeldt, W. H. et al., Transformation of Fatty Acids Catalyzed by Cytochrome P450 Monooxygenase Enzymes of *Candida tropicalis*, Applied and Environmental Microbiology, Oct. 2003, pp. 5992-5999.
Schaverien, C.J., et al., A Well-Characterized Highly Active Lewis Acid Free Olefin Metathesis Catalyst, J. Am. Chem. Soc., 1986, 108, pp. 2771-2773.
Couturier, J-L. et al., A Cyclometalated Arloxy(chloro) neopentylidene-tungsten Complex: A Highly Active and Steroselective Catalyst for the Metathesis of cis- and trans-2-Pentene, Norborene, 1-Methyl-norborene, and Ethyl Pleate, Angew. Chem. Int. Ed. Engl., 31. No. 5, 1992, pp. 628-631.
Schwab, P. et al., A Seris of Well-Defined Metathesis Catalysts-Synthesis of [RuCl2(=CHR')(PR3)2] and Its Reactions, Angew. Chem. Int. Ed. Engl., 34, No. 18, 1995, pp. 2039-2041.
Scholl, M. et al., Synthesis and Activity of a New Generation of Ruthenium-Based Olefin Metathesis Catalysts Coordinated with 1,3-Dimestyl-4,5-dihydroimidazol-2-ylidene Lignads, Organic Letters, vol. 1, No. 6, 1999, pp. 953-956.
Bai, C-X. et al., Lewis-acid assisted cross metathesis of acrylonitrile with functionalized olefins catalyzed by phosphine-free ruthenium carbene comples, Org. Biomol. Chem., vol. 3, 2005, pp. 4139-4142.
Chatterjee, A.K. et al., Formal Vinyl C-H Activationn and Alllylic Oxidation by Okefin Metathesis, Angew. Chem. Int. Ed. Engl., vol. 41, No. 17, 2002, pp. 3171-3174.

* cited by examiner

*Primary Examiner* — Tekchand Saidha
*Assistant Examiner* — Younus Meah
(74) *Attorney, Agent, or Firm* — Smith, Gambrell & Russell, LLP

(57) ABSTRACT

The invention relates to a method for the synthesis of diacids of general formula $ROOC-(CH_2)_n-(CH=CH)_a-(CH_2)_m COOR_1$ in which n and m are identical or different and each represent an integer such that their sum is between 6 and 15, a is an index of 0 or 1, and R and $R_1$ are H or an alkyl radical with 1 to 4 carbon atoms, from long-chain monounsaturated natural fatty acids or esters having at least 10 adjacent carbon atoms per molecule of the general formula $CH_3-(CH_2)_p-CH=CH-(CH_2)_q-COOR$, p and q, being identical or different and representing indices between 2 and 11, wherein said method comprises the first step of oxidizing by fermentation said natural fatty acid or ester, using a microorganism, such as a bacterium, a yeast, or a fungus, into at least one unsaturated dicarboxylic acid or dicarboxylate, the second step of submitting the product from the first step to a metathesis crossed with a compound of formula $R_2OOC-(CH_2)_x-CH=CH-R_3$, in which $R_2$ is H or an alkyl radical with 1 to 4 carbon atoms, x is 0 or 1 or 2, and $R_3$ is H, $CH_3$ or $COOR_2$, in order to obtain the unsaturated compound of formula $ROOC-(CH_2)_q-CH=CH-(CH_2)_x-COOR_2$, and the third optional step of converting the unsaturated compound into a saturated compound by hydrogenation of the double bond.

8 Claims, No Drawings

METHODS FOR THE SYNTHESIS OF FATTY DIACIDS BY THE METATHESIS OF UNSATURATED DIACIDS OBTAINED BY FERMENTATION OF NATURAL FATTY ACIDS

FIELD OF THE INVENTION

The invention is targeted at a process for the synthesis by cross-metathesis of saturated or unsaturated short-chain fatty diacids or diesters starting from a natural monounsaturated fatty acid or fatty ester.

BACKGROUND OF THE INVENTION

The best known unsaturated diacids or diesters are those comprising chains comprising from 4 to 6 carbon atoms, such as the $C_4$ acids maleic acid and fumaric acid, the $C_5$ acids citraconic acid, mesaconic acid and itaconic acid and the $C_6$ acids 2-methyleneglutaric acid and muconic acid. On the other hand, as regards long-chain diacids, the only ones having a degree of importance are dimers, generally obtained by condensation of unsaturated carboxylic acids. The properties, syntheses and uses of these diacids are described in Ullmann's Encylopedia, Vol. A8, pages 533-536.

Saturated diacids are obtained industrially by various methods, all of which, however, exhibit some disadvantages. A great variety of these methods is enlarged upon in the above reference on pages 523-536.

It is possible to distinguish therein methods by degradation, such as ozonolysis or oxidation, of vegetable fatty acids.

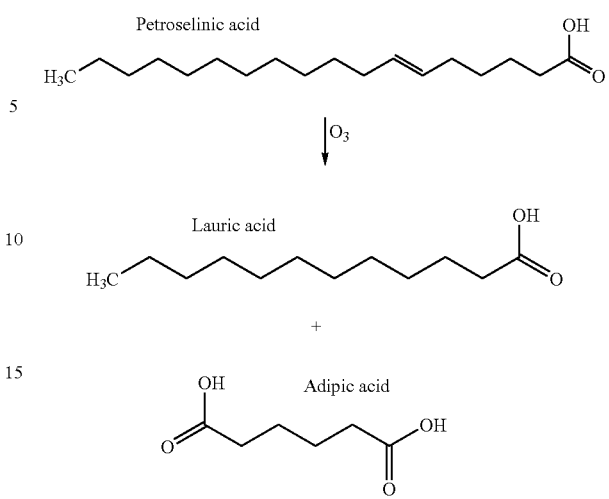

The ozonolysis of oleic acid, of petroselinic acid and of erucic acid makes it possible to respectively produce the diacids comprising 9, 6 and 13 carbon atoms according to the above reaction process for petroselinic acid.

Another example is the cleavage of ricinoleic acid by the action of sodium hydroxide at a temperature of greater than 180° C. This method, used industrially, makes it possible to obtain the diacid comprising 10 carbon atoms. The same method, as illustrated in the scheme below, can be applied to lesquerolic acid and results in the formation of a diacid comprising 12 carbon atoms. This method exhibits the advantage of using renewable starting materials but is restricted essentially to the $C_{10}$ diacid, lesquerolic acid being still not very widespread, and thus this method is relatively little used.

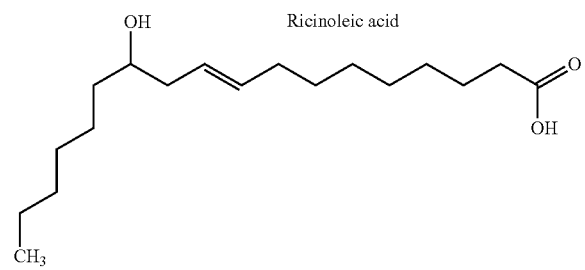

OR

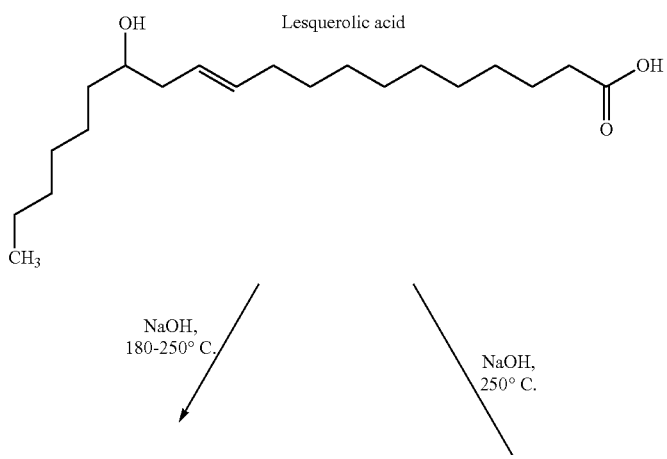

-continued

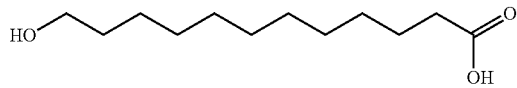

OR

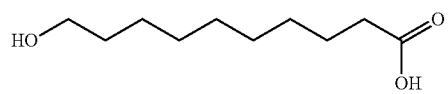

+

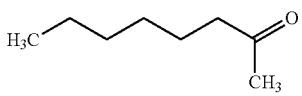

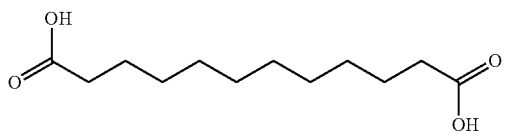

OR

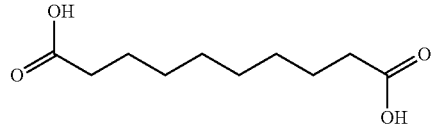

+

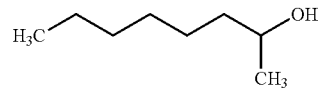

Mention may also be made of the oxidative degradation of monocarboxylic acids by the action of $N_2O_4$. The oxidation of stearic acid makes it possible to obtain a mixture of sebacic acid and of caprylic acid; suberic acid can be obtained from palmitic acid.

It is also possible to obtain diacids from smaller molecules by using variant techniques of carbonylation.

Finally, mention may be made of the fermentation, by a yeast, a fungus or a bacterium, of paraffin hydrocarbon or saturated or unsaturated fatty acid or ester substrates, which makes it possible to oxidize the compounds of the substrate. This method is well known. It is illustrated in particular in the paper by W. H. Eschenfeldt et al., "Transformation of Fatty Acids Catalyzed by Cytochrome P450 Monooxygenase Enzymes of *Candida tropicalis*", and patents FR 2 445 374, U.S. Pat. No. 4,474,882, U.S. Pat. No. 3,823,070, U.S. Pat. No. 3,912,586, U.S. Pat. No. 6,660,505, U.S. Pat. Nos. 6,569,670 and 5,254,466. It makes it possible to obtain numerous diacids of variable chain length.

In the chemical industry and in particular the polymer industry, such as the production of polyamides of diacids/diamines type or of industrial polymers, it is necessary to have available a whole range of saturated or unsaturated diacids. These diacids will constitute starting materials which can in addition be converted to diamines of the same chain length by a simple chemical reaction. The unsaturated diacids will be used as monomers for specialty polymers.

It is therefore necessary to find a type of process which makes it possible to obtain a virtually complete range of saturated or unsaturated diacids and which, in addition, uses renewable materials of natural origin.

DETAILED DESCRIPTION OF THE INVENTION

The object of the invention is a process for the production of a whole range of saturated or unsaturated diacids or diesters of general formula: $ROOC-(CH_2)_n-(CH=CH)_a-(CH_2)_m-COOR$ starting from the fatty acids of natural origin.

In the continuation of the present description, for the clarity of the account, the term "diacid" will be used to denote without distinction the diacid and the diester. This is because, in the process of the invention, the fatty acid can be treated either in its acid form or in its ester form. The change from one form to the other takes place simply by alcoholysis, esterification or hydrolysis.

The solution provided consists in carrying out the operation starting from long-chain natural monounsaturated fatty acids which are oxidized by fermentation to give diacids which are subjected to cross-metathesis with a compound of acrylic type.

Long-chain natural fatty acid is understood to mean an acid resulting from plant or animal sources, including algae, more generally from the plant kingdom, which are thus renewable, comprising at least 10 and preferably at least 14 carbon atoms per molecule.

Mention may be made, as examples of such acids, of the $C_{10}$ acids obtusilic (cis-4-decenoic) acid and caproleic (cis-9-decenoic) acid, the $C_{12}$ acids lauroleic (cis-5-dodecenoic) acid and linderic (cis-4-dodecenoic) acid, the $C_{14}$ acids myristoleic (cis-9-tetradecenoic) acid, physeteric (cis-5-tetradecenoic) acid and tsuzuic (cis-4-tetradecenoic) acid, the $C_{16}$ acid palmitoleic (cis-9-hexadecenoic) acid, the $C_{18}$ acids oleic (cis-9-octadecenoic) acid, elaidic (trans-9-octadecenoic) acid, petroselinic (cis-6-octadecenoic) acid, vaccenic (cis-11-octadecenoic) acid and ricinoleic (12-hydroxy-cis-9-octadecenoic) acid, the $C_{20}$ acids gadoleic (cis-9-eicosenoic) acid, gondoic (cis-11-eicosenoic) acid, cis-5-eicosenoic acid and lesquerolic (14-hydroxy-cis-11-eicosenoic) acid, and the $C_{22}$ acids cetoleic (cis-11-docosenoic) acid and erucic (cis-13-docosenoic) acid.

These various acids result from the vegetable oils extracted from various plants, such as sunflower, rape, castor oil plant, bladderpod, olive, soya, palm tree, coriander, celery, dill, carrot, fennel or Limnanthes alba (meadowfoam).

They also result from the terrestrial or marine animal world and, in the latter case, both in the form of fish or mammals, on the one hand, and of algae, on the other hand. They are in general fats originating from ruminants, from fish, such as the cod, or from marine mammals, such as whales or dolphins.

The invention is targeted at the synthesis of short-chain fatty acids or esters. In the present patent application, short-chain diacids or diesters denote molecules comprising, in the main chain, from 6 to 16 adjacent carbon atoms but which are synthesized starting from a higher diacid and which have a main chain length having a ratio with that of the starting unsaturated fatty acid or ester of between 0.35 and 0.9, preferably of between 0.4 and 0.8 and more preferably still of between 0.5 and 0.7.

The invention is targeted at a process for the synthesis of diacids or diesters of general formula $ROOC-(CH_2)_n-(CH=CH)_a-(CH_2)_m COOR_1$, in which n and m, which are identical or different, each represent an integer such that their sum is between 6 and 15, a is an index equal to 0 or 1 and R and $R_1$ are either H or an alkyl radical comprising from 1 to 4 carbon atoms, starting from long-chain natural monounsaturated fatty acids or esters comprising at least 10 adjacent carbon atoms per molecule, of formula $CH_3-(CH_2)_p-CH=CH-(CH_2)_q-COOR$, in which R represents H or an alkyl radical comprising from 1 to 4 carbon atoms and p and q, which are identical or different, are indices between 2 and 11, which consists, in a first stage, in oxidizing, by fermentation in the presence of a microorganism, said natural fatty acid or ester to give at least one monounsaturated dicarboxylic acid or dicarboxylate, then, in a second stage, in subjecting the product from the first stage to cross-metathesis with a compound of formula $R_2OOC-(CH_2)_x-CH=CH-R_3$, in which $R_2$ is either H or an alkyl radical comprising from 1 to 4 carbon atoms, x is 0, 1 or 2 and $R_3$ is H, $CH_3$ or $COOR_2$, in the last case forming a cyclic or noncyclic molecule, in order to obtain an unsaturated compound of formula $ROOC-(CH_2)_q-CH=CH-(CH_2)_x-COOR_2$, and then, in an optional third stage, in finally converting, by hydrogenation of the double bond, the unsaturated compound to give a saturated compound.

The cross-metathesis is carried out with acrylic acid when $R_2$=H, x=0 and $R_3$=H. In the case where x=1, $R_2$=H and $R_3$=$CH_3$, the compound is $HOOC-CH_2-CH=CH-CH_3$ and is obtained, for example, by hydroxycarbonylation of butadiene. In this case, during the cross-metathesis, propylene is produced and is removed from the reaction medium.

Preferably, when $R_3$ is $COOR_2$, $R_2OOC-(CH_2)_x-CH=CH-R_3$ is a symmetrical molecule with x=0. When $R_3$ is $CH_3$, $R_2OOC-(CH_2)_x-CH=CH-R_3$ reacts with a fatty acid by cross-metathesis and the reaction results in a diacid and a shorter fatty acid but also in propylene. The propylene is removed as it is formed from the reaction medium, which displaces the reaction towards the desired products.

When $R_2OOC-(CH_2)_x-CH=CH-COOR_2$ forms a cyclic molecule, such as maleic anhydride, then the cross-metathesis results in an unsaturated fatty acid also comprising an anhydride functional group. The diacid and the fatty acid can be released by hydrolysis.

In the process of the invention, use is made of fatty acids or esters of natural origin, that is to say present in oils or fats. The latter are in fact composed, in addition to the ester or acid participating in the reaction, of a mixture of esters or acids with similar formulae. By way of examples, sunflower oil comprises, in addition to oleic acid, linoleic acid; castor oil comprises, in addition to ricinoleic acid, both oleic acid and linoleic acid; and rapeseed oil comprises, in addition to oleic acid, simultaneously linoleic acid, linolenic acid and gadoleic acid. The presence of these diunsaturated or polyunsaturated acids is not of major consequence with regard to the progression of the process insofar as the products are separated during the stage following the metathesis reaction.

The first stage is carried out by fermentation in the presence of a microorganism, that is to say using any bacterium, fungus or yeast which makes possible the oxidation of the fatty acid or ester of the feedstock. This fermentation can be carried out in particular in the presence of microorganisms comprising oxidizing enzymes of oxygenase type. It can be carried out, for example, in the presence of a *Candida tropicalis* strain comprising cytochrome P450 monooxygenase enzymes, such as those described in the publication by W. H. Eschenfeldt et al., "Transformation of Fatty Acids Catalyzed by Cytochrome P450 Monooxygenase Enzymes of *Candida tropicalis*", which appeared in Applied and Environmental Microbiology, October 2003, pp 5992-5999, and patents FR 2 445 374, U.S. Pat. No. 4,474,882, U.S. Pat. No. 3,823,070, U.S. Pat. No. 3,912,586, U.S. Pat. No. 6,660,505, U.S. Pat. Nos. 6,569,670 and 5,254,466.

It is possible without distinction to ferment a fatty acid, a fatty ester and a triglyceride. This is because the microorganisms are also capable of metabolizing alcohols and glycerol.

The metathesis reactions employed in the second stage have been known for a long time, even if their industrial applications are relatively limited. Reference may be made, with regard to their use in the conversion of fatty acids (esters), to the paper by J. C. Mol, "Catalytic metathesis of unsaturated fatty acid esters and oil", which appeared in Topics in Catalysis, Vol. 27, Nos. 1-4, February 2004 (Plenum Publishing Corporation).

The catalysis of the metathesis reaction has formed the subject of a great many studies and the development of sophisticated catalytic systems. Mention may be made, for example, of the tungsten complexes developed by Schrock et al., J. Am. Chem. Soc., 108 (1986), 2771, or Basset et al., Angew. Chem., Ed. Engl., 31 (1992), 628. More recently, "Grubbs'" catalysts, which are ruthenium-benzylidene complexes, have appeared (Grubbs et al., Angew. Chem., Ed. Engl., 34 (1995), 2039, and Organic Lett., 1 (1999), 953). These relate to homogeneous catalysis. Heterogeneous catalysts have also been developed which are based on metals, such as rhenium, molybdenum and tungsten, deposited on alumina or silica. Finally, studies have been carried out on the preparation of immobilized catalysts, that is to say of catalysts whose active principle is that of the homogeneous catalyst, in particular ruthenium-carbene complexes, but which is immobilized on an inactive support. The object of these studies is to increase the selectivity of the reaction with regard to the side reactions, such as "homometatheses", between the reactants brought together. They relate not only to the structure of the catalysts but also to the effect of the reaction medium and the additives which may be introduced.

Any active and selective metathesis catalyst can be used in the process of the invention. However, use will preferably be made of catalysts based on ruthenium and on rhenium.

The second stage is illustrated by examples of the synthesis of short-chain fatty diacids are given below. All the mechanisms explained in detail below illustrate, to facilitate the account, the acid form. However, the metathesis is as effective with an ester and often even more effective. In the same way, the schemes illustrate reactions with the cis isomer of the acids (or esters); the mechanisms are equally well applicable to the transisomers.

The reaction process of this second stage employing oleic diacid and acrylic acid is as follows:

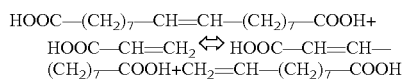

and by consecutive reaction with the acrylic acid, used in excess:

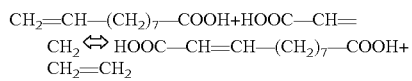

The α,ω-2-undecenedioic acid can, if necessary, be converted to saturated α,ω-undecanedioic acid by hydrogenation according to the following process:

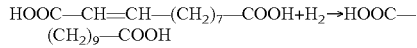

It may be observed that, during the cross-metathesis reaction with an excess of acrylic acid, 9-decenoic acid is formed, which product will result in the formation, by a further cross-metathesis with acrylic acid, of the compound of formula HOOC—CH=CH—(CH$_2$)$_7$—COOH with production of ethylene. An important advantage of the process is thus the absence of coproduct, apart from the ethylene, which is easily removed. The reaction mechanism of this reaction is illustrated in scheme 1 below.

Under certain fermentation conditions, oleic acid is oxidized to give 9-octadecenedioic acid.

The reaction process of this second stage employing this diacid and acrylic acid to produce two identical diacids can be described by the following mechanism:

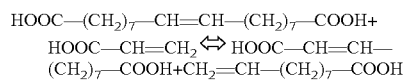

and by consecutive reaction with the acrylic acid, used in excess:

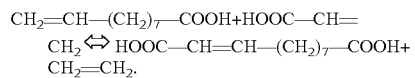

Scheme 1

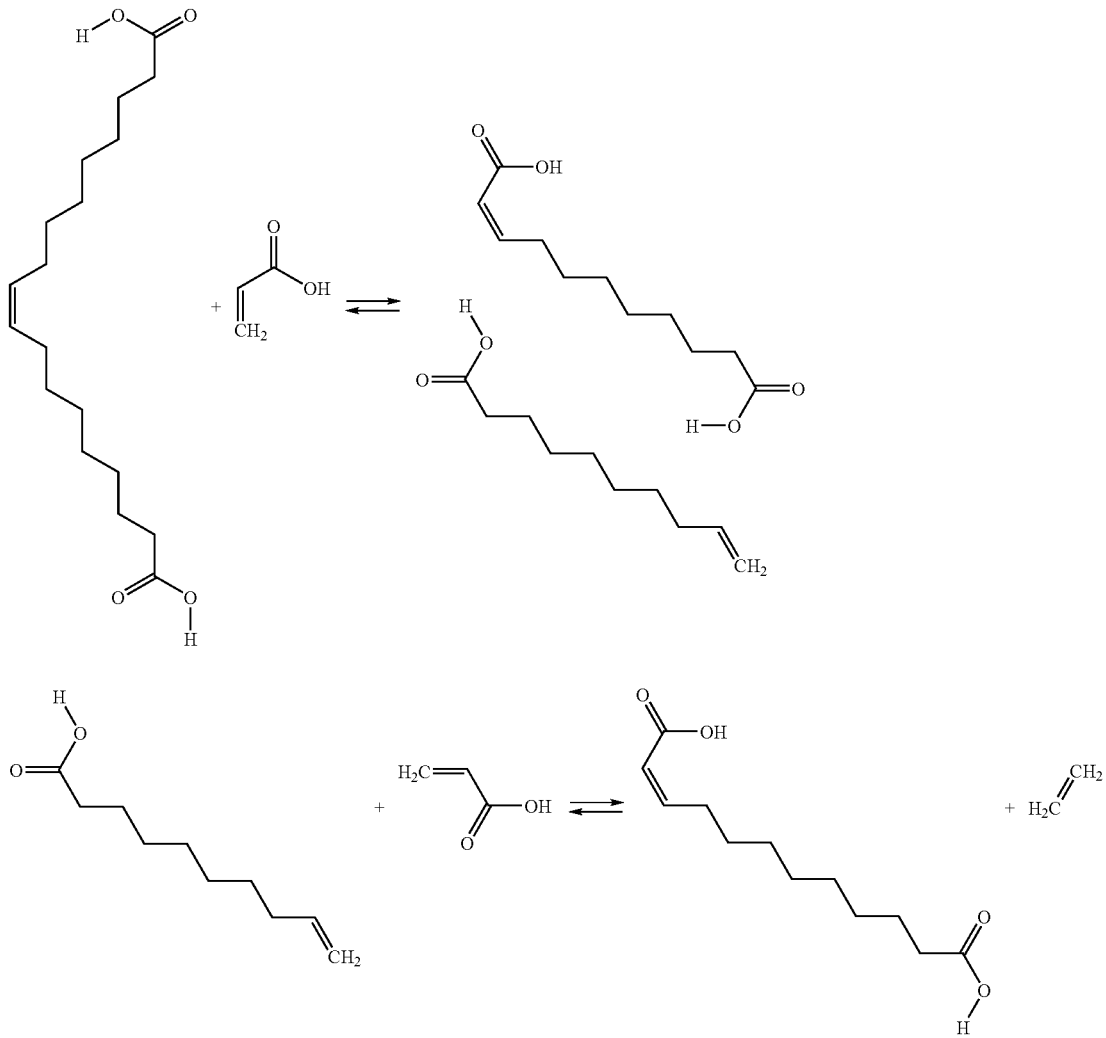

Under certain fermentation conditions, macadamia oil or sea buckthorn oil is partially oxidized to give a $C_{16}$ diacid, α-ω-7-hexadecenedioic acid, starting from the palmitoleic acid present in these oils.

Scheme 2

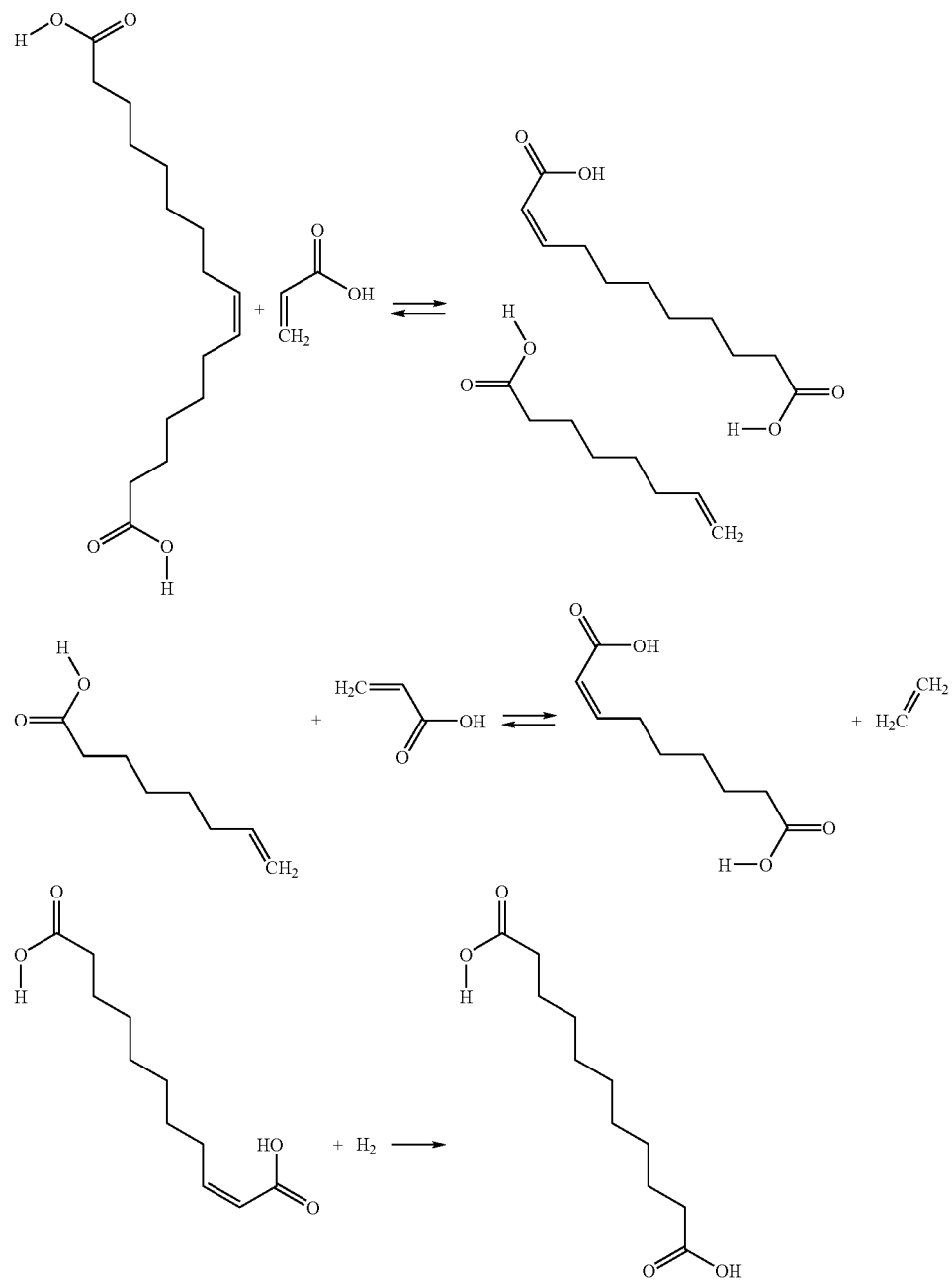

The reaction process of this second stage employing this diacid and acrylic acid in order to produce two different diacids can be described by the following mechanism:

HOOC—$(CH_2)_5$—CH=CH—$(CH_2)_7$—COOH+
HOOC—CH=$CH_2$ ⇔ HOOC—CH=CH—
$(CH_2)_7$—COOH+$CH_2$=CH—$(CH_2)_5$—COOH and by consecutive reaction with the acrylic acid, used in excess:

$CH_2$=CH—$(CH_2)_5$—COOH+HOOC—CH=
$CH_2$ ⇔ HOOC—CH=CH—$(CH_2)_5$—COOH+
$CH_2$=$CH_2$.

Palmitoleic acid can be converted during the fermentation to give α,ω-7-hexadecenedioic acid. The second stage of the process will result in two α,ω-diacids with different lengths, according to the following process:

HOOC—$(CH_2)_5$—CH=CH—$(CH_2)_7$—COOH+
HOOC—CH=$CH_2$ ⇔ HOOC—CH=CH—
$(CH_2)_7$—COOH+$CH_2$=CH—$(CH_2)_5$—COOH and by consecutive reaction with the acrylic acid, used in excess:

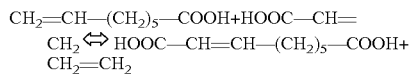

These two acids can be hydrogenated to form $C_{11}$ and $C_9$ diacids respectively.

Petroselenic acid is converted during the fermentation to give α,ω-6-octadecenedioic acid. The second stage of the process will result in two α,ω-diacids with different lengths, according to the following process:

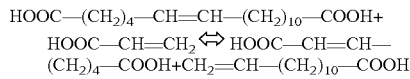

and by consecutive reaction with the acrylic acid, used in excess:

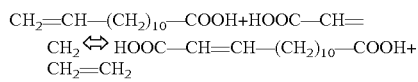

Gadoleic acid is converted during the fermentation to α,ω-9-eicosenedioic acid. The second stage of the process will result in two α,ω-diacids with different lengths, according to the following process:

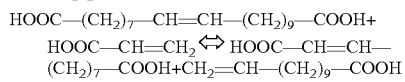

and by consecutive reaction with the acrylic acid, used in excess:

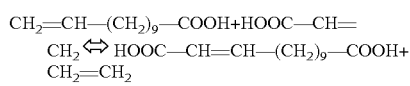

The process of the invention is illustrated by the following examples.

EXAMPLES

Example 1

Fermentation of Oleic Acid

In this example, a yeast comprising oxygenase enzymes will be cultured, at pH=7, in a deionized water medium comprising sorbitol, trace elements, urea and oleic acid. The mixture will subsequently be sterilized at 120° C. for 15 minutes. A yeast strain will subsequently be inoculated into the culture medium. The culture will be maintained at 30° C. A sodium hydroxide solution will be added continuously in order to maintain the pH at 7-7.5. After culturing for 48 hours, the unsaturated diacid will be recovered by extraction with diethyl ether. After removing the solvent by evaporation, crystals will be recovered which, after recrystallization, have a melting point of 69° C., that is to say equivalent to that described for 9-octadecenedioic acid.

Example 2

Fermentation of Erucic Acid

Example 1 will be reproduced with erucic acid. 9-Docosenedioic acid will be obtained.

Example 3

Cross-Metathesis of 9-Octadecenedioic Acid with Acrylic Acid

This example illustrates the synthesis of the $C_{11}$ diacid starting from the 9-octadecenedioic acid obtained in example 1 in a second stage consisting of a cross-metathesis with acrylic acid. Use will be made, for this reaction, of a complex catalyst of bispyridine-ruthenium type analogous to that described in the publication by Chen-Xi Bai et al., Org. Biomol. Chem., (2005), 3, 4139-4142. The reaction will be carried out in $CH_2Cl_2$, with a molar concentration of acrylic acid two times greater than that of the 9-octadecenedioic add, at a temperature of the order of 80° C., for 12 hours, in the presence of the catalyst at a concentration of 1 mol % with respect to the 9-octadecenedioic acid. The product obtained, in its ester or acid form, can be hydrogenated according to a conventional process with a yield of 100%.

Example 4

Cross-Metathesis of 9-Docosenedioic Acid

Example 3 will be reproduced with the diacid of example 2, 9-docosenedioic acid. A substantially equimolar yield of 2-undecenedioic acid and 2-pentadecenedioic acid will be obtained.

Example 5

Cross-Metathesis of the Unsaturated $C_{18}$ Diester with Methyl Acrylate 170 mg of methyl 9-octadecenedioate (0.5 mmol), 170 mg of methyl acrylate (2 mmol) and 10 ml of toluene distilled over sodium/benzophenone are charged to a 50 ml Schlenk tube purged with nitrogen. Heating is carried out to 100° C. and then 0.3 mg ($0.5 \times 10^{-3}$ mmol) of Hoveyda-Grubbs catalyst $2^{nd}$ Generation (1,3-bis(2,4,6-trimethylphenyl)-2-imidazolidinylidene)dichloro(o-isopropoxyphenylmethylene)ruthenium) available from Aldrich, dissolved in 2 ml of toluene, is added with a syringe and a syringe driver over a period of 2 h with magnetic stirring. At the end of the addition, reaction is allowed to take place for 4 hours. The reaction mixture is analyzed by gas chromatography. The conversion of the unsaturated diester is greater than 99%. The methyl 2-undecenedioate yield is 95%.

What is claimed is:

1. A process for the synthesis of diacids or diesters of general formula $ROOC—(CH_2)_n—(CH=CH)_a—(CH_2)_m COOR_1$, wherein n and m, which are identical or different, each represent an integer such that their sum is between 6 and 15, a is 0 or 1 and R and $R_1$ are either H or an alkyl radical comprising from 1 to 4 carbon atoms, starting from long-chain natural monounsaturated fatty acids or esters comprising at least 10 adjacent carbon atoms per molecule, of formula $CH_3—(CH_2)_p—CH=CH(CH_2)_q—COOR$, in which R represents H or an alkyl radical comprising from 1 to 4 carbon atoms and p and q, which are identical or different, are between 2 and 11, comprising:

oxidizing, in a first step, by fermentation by a microorganism comprising oxygenase enzymes, said long-chain natural monounsaturated fatty acid or ester to give at least one monounsaturated dicarboxylic acid or dicarboxylate, and thereafter, subjecting, in a second step, the product from the first step to cross-metathesis with a compound of formula $R_2OOC—(CH_2)_x—CH=CH—R_3$, in which $R_2$ is either H or an alkyl radical comprising from 1 to 4 carbon atoms, x is either 0 or 1 or 2 and $R_3$ is H, $CH_3$ or $COOR_2$, to obtain an unsaturated compound of formula $ROOC—(CH_2)_q—CH=CH—(CH_2)_x—COOR_2$, and then, in an optional third step, converting, by hydrogenation of the double bond in the unsaturated compound to give a saturated compound, wherein the diacids or diesters of general formula $ROOC-(CH_2)_n-(CH=CH)_a-(CH_2)_m COOR_1$ comprise in the main chain from 6 to 16 adjacent carbon atoms and have a main chain length having a ratio with that of the starting long-chain natural monounsaturated fatty acids or esters of formula $CH_3-(CH_2)_p-CH=CH-(CH_2)_q-COOR$ between 0.35 and 0.9.

2. The process as claimed in claim 1, wherein the oxidizing by fermentation is carried out in the presence of a *Candida tropicalis* strain comprising cytochrome P450 monooxygenase enzymes.

3. The process as claimed in claim 1, wherein the metathesis is carried out with acrylic acid.

4. The process as claimed in claim 3, wherein a catalyst based on ruthenium and rhenium is used in said cross-metathesis.

5. The process as claimed in claim 1, wherein 2-undecenedioic acid of formula $HOOC-CH=CH-(CH_2)_7COOH$ is synthesized from a long-chain natural monounsaturated fatty acid or ester comprising oleic acid.

6. The process as claimed in claim 1, wherein 2-undecenedioic acid and 2-pentadecenedioic acid are synthesized from a long-chain natural monounsaturated fatty acid or ester comprising erucic acid.

7. The process as claimed in claim 1, wherein said microorganism comprising oxygenase enzymes is selected from the group consisting of a bacterium, a fungus, and a yeast.

8. The process claimed in claim 1, wherein in the second step, when the alkyl radical is $COOR_2$, a cyclic or noncyclic molecule is formed.

\* \* \* \* \*